United States Patent [19]

Albisser et al.

[11] Patent Number: 4,601,707
[45] Date of Patent: Jul. 22, 1986

[54] INSULIN INFUSION DEVICE

[76] Inventors: Anthony M. Albisser, 52 Wndover Road, Toronto, Ontario, M8X 2L3; Bernard Zinman, 41 Pinnacle Road, Willowdale, Ontario, M2L 2V6, both of Canada

[21] Appl. No.: 267,364

[22] Filed: May 22, 1981

[30] Foreign Application Priority Data

Jun. 3, 1980 [CA] Canada ................................. 353268

[51] Int. Cl.$^4$ ............................................. A61M 5/14
[52] U.S. Cl. .................................... 604/131; 604/151; 128/DIG. 12; 222/101
[58] Field of Search ........... 128/213 R, 214 E, 214 F, 128/260, 261, 273, DIG. 12; 604/131, 151, 153, 154, 155; 222/101, 102

[56] References Cited

U.S. PATENT DOCUMENTS

| | | |
|---|---|---|
| 2,605,765 | 8/1952 | Kollsman . |
| 3,151,616 | 10/1964 | Selfon .................... 604/131 |
| 3,198,385 | 8/1965 | Maxwell .................... 128/DIG. 12 |
| 3,384,080 | 5/1968 | Muller .......................... 128/214 F |
| 3,469,578 | 9/1969 | Bierman . |
| 3,685,697 | 8/1972 | Caslow et al. . |
| 3,858,581 | 1/1975 | Kamen . |
| 3,886,938 | 6/1975 | Szabo . |
| 4,013,074 | 3/1977 | Siposs .................... 128/260 |
| 4,059,110 | 11/1977 | Wuthrich et al. . |
| 4,077,405 | 3/1978 | Haerten et al. . |
| 4,108,177 | 8/1978 | Pistor . |
| 4,155,362 | 5/1979 | Jess . |
| 4,201,207 | 5/1980 | Buckles et al. ................... 128/214 F |
| 4,300,554 | 11/1981 | Hessberg et al. . |
| 4,313,439 | 2/1982 | Babb et al. ...................... 128/214 F |
| 4,320,757 | 3/1982 | Whitney et al. ................. 128/214 F |
| 4,525,164 | 6/1985 | Loeb et al. .......................... 604/131 |

FOREIGN PATENT DOCUMENTS

| | | |
|---|---|---|
| 28096 | 11/1887 | Canada . |
| 0019817 | 10/1980 | European Pat. Off. . |
| 2721752 | 11/1978 | Fed. Rep. of Germany . |
| 2916835 | 2/1980 | Fed. Rep. of Germany . |
| 2942213 | 4/1980 | Fed. Rep. of Germany . |
| 2387046 | 12/1978 | France .......................... 128/214 R |
| WO81/01658 | 6/1981 | PCT Int'l Appl. . |
| 1554083 | 10/1979 | United Kingdom . |
| 2035094B | 6/1980 | United Kingdom . |

Primary Examiner—Lee S. Cohen
Attorney, Agent, or Firm—Murray and Whisenhunt

[57] ABSTRACT

The invention provides an improved device for the injection of medicament such as insulin subcutaneously. The device provides discrete regular injections from an end of a tube containing medicament. The discrete amounts of the injections are programmed to provide a basal injection rate and additional discrete injections can be provided at the user's discretion so that the user has sufficient flexibility to control sudden demands for medicament while nevertheless leaving the basal injection schedule essentially uninterupted.

8 Claims, 5 Drawing Figures

INSULIN INFUSION DEVICE

This invention relates to a device for controlled subcutaneous injection of medicaments such as insulin in discrete quantities at selected timed intervals to provide a user's daily requirement at a basal rate, and for permitting additional discrete quantities at times of increased need at the discretion of the user.

Although the present invention will be described for use with the treatment of diabetes mellitus, it will be apparent that other treatments requiring similar extended periods of injection of a medicament are possible using the same device.

The current standard therapy of insulin dependent diabetics with depot insulin injections fails to normalize entirely plasma glucose levels as well as the other metabolic abnormalities of the disease. The consequences of this imperfect metabolic regulation are believed to significantly contribute to the long term chronic and disabling complications of diabetes mellitus. Recent studies employing crude mechanical devices designed to infuse insulin continuously or by multiple small injections to meet fluctuations in daily requirements have shown a marked improvement in glycemic and other metabolic and hormonal profiles in diabetic subjects.

Although such mechanical devices are an improvement over daily injections, they nevertheless suffer from disadvantages which the present invention is intended to overcome.

For a mechanical device to be acceptable for subcutaneous injection of insulin and the like, the device should be compact, and readily located on the patient adjacent sites where a needle can be inserted subcutaneously. Preferably the device should be capable of providing a basal rate of injection while at the same time being capable of use to provide discrete additional doses at the patient's discretion and as directed. The device should also provide a visible and readily recognized indication of whether or not the device is working as well as the amount of medicament injected and the amount remaining in the device. Preferably the user should be able to over-ride the driving mechanism of the device so that in the event of complete failure, the device can be used manually for sufficient time to permit the user to seek help.

Accordingly, the invention provides an improved device for the injection of medicament such as insulin subcutaneously. Medicament is squeezed from a tube to provide a basal injection rate. Additional medicament can be provided at the user's discretion thereby providing the user with sufficient flexibility to control sudden demands for medicament while nevertheless leaving the basal injection schedule essentially uninterrupted.

The invention will be better understood with reference to the following description taken in combination with the drawings, in which.

Figures 1, 5:
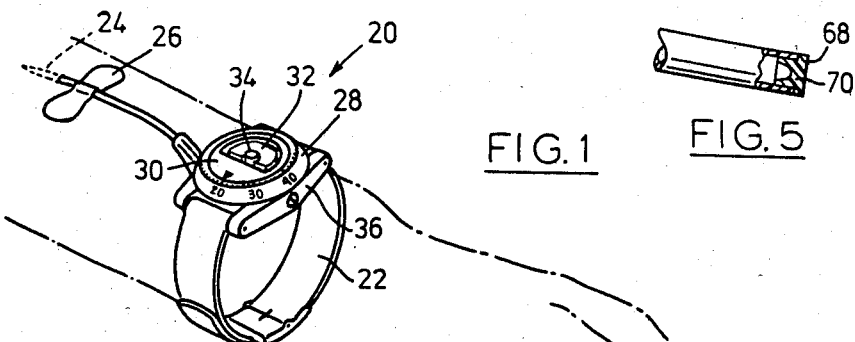
FIG. 1 is a perspective and somewhat diagrammatic view of a preferred embodiment of a device in position on a user's wrist.
FIG. 5 is a sectional side view of the end of a tube used in an alternative embodiment of the invention and drawn to a larger scale than FIG. 1.

Reference is first made to FIG. 1 which illustrates a preferred embodiment of the device designated generally by the numeral 20 and shown positioned on a user's wrist. In this embodiment the device is attached by a band 22 and is feeding insulin (or other medicament) subscutaneously by way of a needle 24. The needle is attached in conventional fashion by adhesive strapping 26. It will be seen that the device includes a fixed scale 28 cooperating with a moving element 30 having a pointer adjacent the scale. This pointer indicates the number of discrete pulses of insulin available from the device and not yet used. With each pulse the pointer moves one division of the scale and these pulses are timed as will be described. Also visible in FIG. 1 is a small handle 32 which can be lifted from the plane of the dial 28 to rotate a spindle 34 for winding a clockwork mechanism thereby storing energy for use in moving insulin to the needle 24. The handle is arranged so that it must be lifted out before it can be turned so that it over-rides an escapement mechanism which is to be described. Such arrangements are conventional in clockwork machinery generally. For instance a similar arrangement is used when setting the time on a mechanical clock.

As also seen in FIG. 1, the housing of the device contains a small flush button 36 which permits the user to over-ride an electronic timing circuit to provide a desired number of extra pulses of insulin which pulses are readily visible by the movement of the element 30 and associated pointer around the scale 28. This permits the user to receive increased dosage of insulin prior to meals and at other times of increased demand. However such extra dosing will not affect the basal rate indicated by prior programming of the device as will be described.

Figure 2:
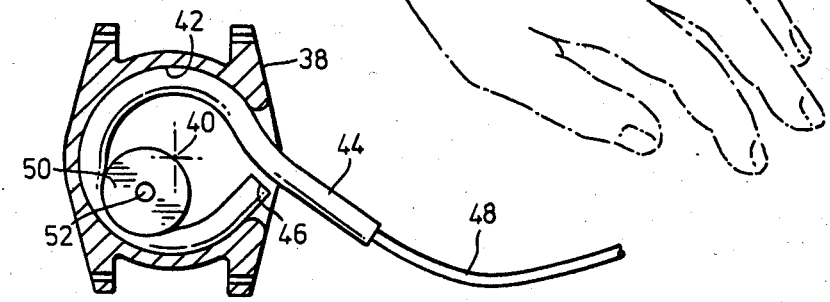
FIG. 2 is a sectional view of the device showing the relationship between a nip and a tube containing medicament such as insulin.

Turning now to FIG. 2, which is a section of the device shown in FIG. 1, there is a housing 38 disposed about a central axis 40 and defining a cavity having an outer wall 42 which is disposed about the axis 40. This wall is positioned to restrain a flexible tube 44 of larger inside diameter having a vented or open end 46 and connected to a further tube 48 of substantially smaller inside diameter leading to the needle 24 (FIG. 1). A roller 50 is held in position by a structure not shown in FIG. 2 on a pin 52 and is restrained to move about the axis 40 forming a nip between the roller 50 and the outer wall 42. As will be described, the roller is made to move about axis 40 to displace liquid contained between the nip and the needle through the needle causing subcutaneous injection. The inside diameter of the tube 44 is chosen so that delivery from the needle corresponds to the calibration on the fixed scale 28.

Figure 3:
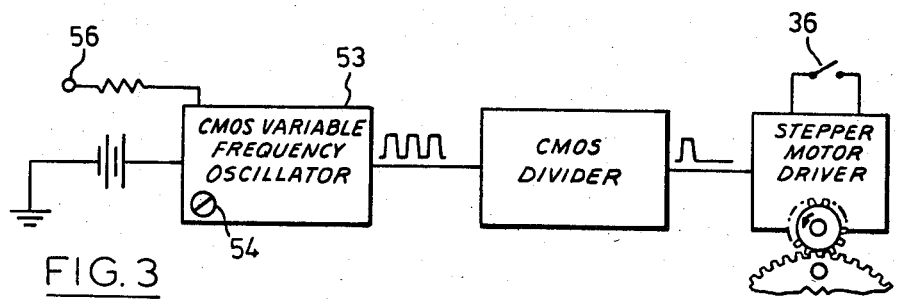
FIG. 3 is a schematic diagram illustrating the control mechanism used in the device.

A preferred embodiment of a control circuit is shown diagrammatically in FIG. 3. A CMOS (complementary metal oxide semiconductor) variable frequency oscillator is used to create a square waveform which is fed to a CMOS divider. The frequency of the waveform can be varied over a range of 8 to 1 by a control 54 and it is possible to identify the frequency from a test point 56. The waveform leaving the oscillator 53 is shown diagrammatically in FIG. 3 and the divider then reduces the frequency resulting in intermittent pulses which are then fed to a stepper motor driver. An associated motor drives a pinion 58 which is in engagement with a gear wheel 60. The gear wheel carries the pin 52 (FIG. 2)

associated with the roller so that each impulse from the CMOS divider causes the stepper motor to advance the pinion 58 a discrete amount which in turn moves the gear wheel 60 and results in the injection as previously described. As a result the nip moves around the housing 38 sufficient to cause medicament to be injected subcutaneously.

It will be appreciated that the power required to drive the stepper motor may not be available from a miniature battery of the type used for the electronics necessary to drive the variable frequency oscillator and the divider. Although the connections have not been shown, it is obvious that additional power could be provided to the stepper motor by way of a separate battery or any other convenient means. If necessary, an additional battery for this purpose could be attached to the strap 22 of the structure shown in FIG. 1 or remotely as preferred.

Although the preferred embodiment has many advantages, it will be appreciated that it can take different forms. For instance it could be attached to a patient's abdomen which may be advantageous in some instances but of course makes the visual display less convenient than that shown in FIG. 1.

Figure 4:
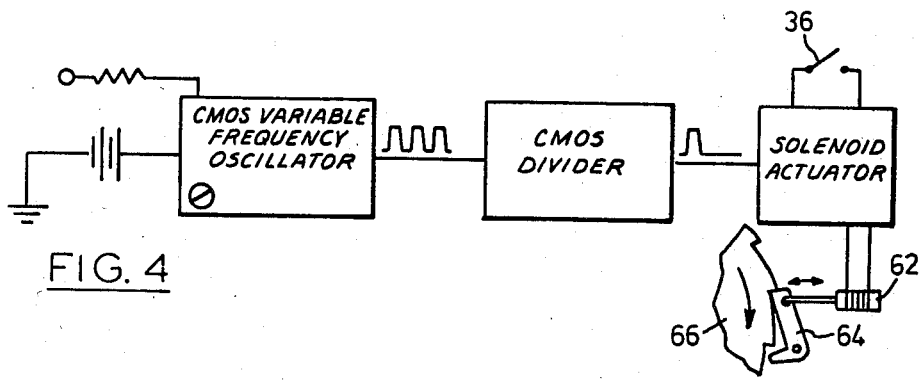
FIG. 4 is a view similar to FIG. 3 illustrating an alternative embodiment of the control system.

The structure associated with the stepper motor and roller forms in effect an escapement mechanism. An alternative escapement mechanism is shown in FIG. 4. As with the structure shown in FIG. 1, a variable frequency oscillator and divider are used but the pulse provided by the divider is fed to a solenoid actuator which again may be fed by an independent battery source. This actuator operates a solenoid 62 and a mechanical rocking escapement element 64. This element is associated with a wheel 66 which, with respect to the roller 50 (FIG. 2) corresponds to the gear wheel 60 shown in FIG. 3.

To use this embodiment of the inventive devices, a user would take a new disposable tube and needle assembly from a sterile package and insert the pump tube into the housing to take up the position shown in FIG. 2. The user would then advance the handle 32 (FIG. 1) in a counter-clockwise direction until the pointer on the element 30 indicated the number of units to be dispensed during the following 24 hours. The protective needle guard would then be removed from the needle and the needle inserted into an insulin vial before advancing the timing mechanism (and the arrow on element 30 to zero) to expel the air in the tube into the insulin vial. After this has been done, the element would be reversed to aspirate the total daily dose of insulin required ending when the pointer had reached a figure on the scale 28 correspondong to the anticipated need for the day.

Following this the user would then insert the needle into the subcutaneous tissues, tape it in place and tie the band 22 about the arm in watch-like fashion. Alternatively it could be attached by adhesive or by a belt to the abdomen.

The advancement of the mechanism would depend on the escapement mechanism so that at nominal settings a 1 unit quantity of insulin would be administered each hour. For patients requiring more insulin, the fundamental frequency of the timer device can be adjusted by the control 54 (FIG. 3) so that it advances at a rate slightly more often than once an hour. Conversely, for a patient requiring slightly less insulin, this electronic timer can be adjusted in such a way that intermittent injections in the basal period occur less than once per hour. These adjustments would be made by technical staff at the direction of the user's medical adviser.

The propulsion mechanism of the pump includes a watch or clock spring which is rewound each day by the patient during the filling cycle. It is biased in such a way that the spring is always under tension. The control of the device by the electronic timer is with a safety escapement mechanism which prevents the accidental injection of the entire contents of the pump tube so the device can only fail safe by not injecting insulin. Lifting the handle 32 (FIG. 1) overcomes this safety feature and allows the device to be set manually.

At mealtime the device is actuated by depressing the button 36 which is mounted flush with the surface of the housing to activate the electronic escapement mechanism and to advance the device by 1 calibrated graduation, thereby administering 1 unit of insulin. Patients will be instructed by their physicians initially on the use of he device and will adapt their insulin regimen according to their dietary habits. In this way, meal insulin may involve amounts of insulin ranging between 2 and 15 units, depending on the type of the meal and the patient's requirements.

This is a novel device which is an improvement over existing devices in that it uses an electronically controlled escapement mechanism for the control of the administration of a drug. The device does not include an external reservoir to contain the drug and only contains enough drug for a single day's use. On successive days, the patient replaces the disposable portion, recharges it and resets the mechanism. The adjustment of the electronic timer mechanism allows the establishment of a suitable basal rate. In this preferred embodiment the pump tube is vented and only forms a reservoir in so far that it contains medicament between the nip and the needle. Furthermore, because of the intermittent application of insulin, the device is not suitable for the treatment of diabetes by intravenous insulin delivery. During the long time between pulses, blood would diffuse into the needle and eventually clot in situ preventing the pump from advancing or distributing insulin and there is a risk that the pump will overcome the resistance of the clot and inject this into the circulation with adverse affects. It is also foreseen that the use of a needle in the blood vessel would not be an appropriate method for gaining access thereto, but it is foreseen that in some circumstances, a soft rubber catheter in lieu of the needle could be placed in the subcutaneous tissue for the delivery of insulin for longer periods of time than a day. This particular alternative configuration may be useful in animal studies.

Alternative pump tube structures could be used within the scope of the invention. The vented end of the tube could include a one-way valve or flap to allow air to be expelled but which limits air flow back into the tube. In this case the tube would simply collapse behind the roller as medicament is dispensed. Another pump tube can be sealed at the end as seen in FIG. 5. In this embodiment the end of the tube is closed by a small stopper or bung 68 having a thin wall or septum 70.

In use the pump tube shown in FIG. 5 is filled using a syringe and needle which pierces the septum. Once full of medicament, the pump tube is placed in the device and after reassembly, the over-ride is used to move the pointer to register with the number if discrete injections required. The outlet tube 48 is then connected for injecting the remaining medicament in the same manner as described previously. Because the tube is not vented it will simply collapse behind the roller as the medicament is dispensed in front of the roller.

These and other modifications are within the scope of the invention as described and claimed.

We claim:

1. A portable device for the subcutaneous administration of liquid medicament, said device comprising:
   a flexible tube for containing the entire supply of a predetermined quantity of liquid medicament to be administered during a predetermined period of operation of the device, said flexible tube being in fluid communication with catheter means for effecting subcutaneous administration of said liquid medicament;
   housing means for containing said flexible tube;
   roller means coupled to said housing means, said roller means cooperating with said housing means to form a nip, said roller means and said housing means being movable relative to each other for squeezing said flexible tube in said nip for expelling said predetermined quantity of liquid medicament through said catheter means;
   drive means for effecting said relative movement between said housing means and said roller means for forcing said liquid medicament out through said catheter means;
   control means for operating said drive means, said medicament being expelled from said flexible tube at a rate sufficient to effect said subcutaneous administration of said liquid medicament.

2. A portable device as claimed in claim 1, wherein said roller means is coupled to said housing means such that said nip is permitted to move in an arcuate path.

3. A portable device as claimed in claim 1, in which said flexible tube has first and second ends, said catheter means being in fluid communication with said first end, said second end being vented.

4. A portable device for the subcutaneous administration of liquid medicament, said device comprising:
   a flexible tube for containing the entire supply of a predetermined quantity of liquid medicament to be administered during a predetermined period of operation of said device, said flexible tube being in fluid communication with catheter means for effecting subcutaneous administration of said liquid medicament;
   housing means for containing said flexible tube, said housing means having an arcuate wall;
   roller means coupled to said housing means, said roller means cooperating with said arcuate wall to define a nip, said roller means and said arcuate wall being movable relative to each other for squeezing said flexible tube in said nip for expelling said predetermined quantity of liquid medicament through said catheter means;
   drive means for effecting said relative movement between said arcuate wall and said roller means for forcing said liquid medicament out through said catheter means;
   control means for operating said drive means, said medicament being expelled from said flexible tube at a rate sufficient to effect said subcutaneous administration of said liquid medicament.

5. A portable device for the subcutaneous administration of liquid medicament, said device comprising:
   a flexible tube for containing the entire supply of a predetermined quantity of liquid medicament to be administered during a predetermined period of operation of the device, said flexible tube being in fluid communication with a needle at one end of said flexible tube;
   a housing disposed about an axis and defining a cavity having an arcuate wall disposed at a substantially constant radial distance from said axis, said housing retaining said flexible tube containing said entire supply of predetermined quantity of liquid medicament;
   roller means rotatably mounted about said axis, said roller means and said wall defining a nip, said roller means and said wall being movable relative to each other for squeezing said tube in said nip for expelling said predetermined quantity of liquid medicament through said needle;
   signal generation means for producing timing signals; and
   means responsive to said timing signals for effecting said relative movement between said roller means and said wall to expel said medicament from said flexible tube at a rate sufficient to effect said subcutaneous administration of said liquid medicament.

6. A portable device for the subcutaneous administration of liquid medicament, said device comprising:
   an electronic timer providing timed pulses;
   a clockwork drive mechanism;
   escapement means responsive to said timed pulses for releasing mechanical energy pulses from said clockwork drive mechanism;
   a flexible tube for containing the entire supply of a predetermined quantity of liquid medicament to be administered during a predetermined period of operation of said device, said flexible tube being in fluid communication with catheter means for effecting subcutaneous administration of said liquid medicament;
   housing means containing said flexible tube, said housing means having an arcuate wall;
   roller means coupled to said housing means, said roller means and said arcuate wall defining a nip, said roller means and said arcuate wall being movable relative to each other for squeezing said tube in said nip for expelling said predetermined quantity of liquid medicament through said catheter means;
   drive means coupled to said escapement means for effecting said relative movement between said arcuate wall and said roller means for forcing said liquid medicament out through said catheter means, said drive means effecting said relative movement over a discrete distance in response to each energy pulse;
   means coupled to said escapement means for overriding said electronic timer to provide additional mechanical energy pulses, thereby causing additional discrete amounts of medicament to be expelled from said flexible tube on demand by the user.

7. A method for subcutaneously delivering a fluid medication to a patient, said method comprising:
   providing catheter means and a device for the subcutaneous administration of liquid medicament, said device comprising a flexible tube for containing the entire supply of a predetermined quantity of liquid medicament to be administered during a predetermined period of operation of the device, said flexible tube being in fluid communication with the catheter means for effecting subcutaneous administration of said liquid medicament, housing means containing said flexible tube, roller means coupled to said housing means, said roller means cooperating with said housing means to form a nip, said roller means and said housing means being movable relative to each other for squeezing said flexible tube in said nip for expelling said predetermined quantity of liquid medicament through said catheter means, drive means for effecting said relative movement between said housing means and said roller means for forcing said liquid medicament out through said catheter means, and control means for operating said drive means, said medicament being expelled from said flexible tube at a rate sufficient to effect said subcutaneous administration of said liquid medicament; connecting the catheter means subcutaneously to the patient and restraining the device on the patient adjacent the catheter means; and actuating said control means to operate said drive means, whereby said drive means effects said relative movement between said housing means and said roller means to force said liquid medicament out through said catheter means to effect subcutaneous administration of said liquid medicament to said patient.

8. A method as claimed in claim 7, and further comprising the steps of selectively overriding said control means and actuating said drive means to expel a further predetermined volume of medication in response to demand by the user.

* * * * *